(12) United States Patent
Hu

(10) Patent No.: US 11,896,454 B2
(45) Date of Patent: Feb. 13, 2024

(54) THERAPEUTIC POSITION VERIFYING TOOL FOR ORAL APPLIANCES

(71) Applicant: Jerry C. Hu, DDS Family Dentistry, LLC, Soldotna, AK (US)

(72) Inventor: Jerry C. Hu, Soldotna, AK (US)

(73) Assignee: Jerry C. Hu, DDS Family Dentistry, LLC, Soldotna, AK (US)

( * ) Notice: Subject to any disclaimer, the term of this patent is extended or adjusted under 35 U.S.C. 154(b) by 939 days.

(21) Appl. No.: 16/573,932

(22) Filed: Sep. 17, 2019

(65) Prior Publication Data

US 2020/0129278 A1 Apr. 30, 2020

Related U.S. Application Data

(60) Provisional application No. 62/737,696, filed on Sep. 27, 2018.

(51) Int. Cl.
*A61C 19/05* (2006.01)
*A61B 5/00* (2006.01)
*A61C 19/06* (2006.01)
*A61F 5/56* (2006.01)

(52) U.S. Cl.
CPC ............ *A61C 19/05* (2013.01); *A61B 5/7275* (2013.01); *A61C 19/06* (2013.01); *A61F 5/566* (2013.01)

(58) Field of Classification Search
CPC ..... A61B 5/1072; A61B 5/1076; A61B 5/481; A61B 5/4812; A61B 5/4818; A61B 5/7275; A61B 5/4557; A61B 5/097; A61B 17/8071; A63B 2071/086; A63B 71/085; A61C 19/045; A61C 19/05; A61C 19/06; A61C 11/00; A61C 7/08; A61C 7/36; A61C 9/0006; A61F 2/2803; A61F 2002/30991; A61F 5/56; A61F 5/566; A61F 2005/563; Y10S 602/902
USPC .......................... 128/848, 859, 861; 602/902
See application file for complete search history.

(56) References Cited

U.S. PATENT DOCUMENTS

| | | | | |
|---|---|---|---|---|
| 5,823,194 A | * | 10/1998 | Lampert | A61F 5/566 128/859 |
| 5,829,441 A | * | 11/1998 | Kidd | A61F 5/566 128/859 |
| 5,868,138 A | * | 2/1999 | Halstrom | A61F 5/566 128/859 |
| 8,226,407 B2 | | 7/2012 | Tanewinkel et al. | |

(Continued)

*Primary Examiner* — Ophelia A Hawthorne
*Assistant Examiner* — Michael Milo

(57) ABSTRACT

A therapeutic position verifying tool is a semi-custom oral appliance equipped with adjustment assemblies for setting trial occlusion dimensions during a process of fitting a patient for an oral appliance. The oral appliance is fabricated from a polymer such as control-cured PMMA. The adjustment assemblies enable the vertical, anterior-posterior and lateral occlusion dimensions to be set. Occlusion dimensions are measured directly with a pharyngometer or indirectly with a bite registration method. The measurements are transferred to the tool by setting the tool to the measured dimensions using the adjustment assembly. When a target therapeutic position for a patient is found, the patient tests the position during the night with a Polysomnogram (PSG) or Home Sleep Test (HST). The use of the tool in verifying a therapeutic position for an oral appliance eliminates much of the time-consuming process of titrating the appliance to the patient.

19 Claims, 13 Drawing Sheets

(56) References Cited

U.S. PATENT DOCUMENTS

| | | | |
|---|---|---|---|
| 8,550,816 B2 | 10/2013 | Hanewinkel et al. | |
| 8,684,006 B2 | 4/2014 | Levendowski et al. | |
| 2006/0174897 A1* | 8/2006 | Sarkisian | A61F 5/566 128/859 |
| 2006/0196512 A1* | 9/2006 | Gaskell | A61F 5/566 128/859 |
| 2007/0209666 A1* | 9/2007 | Halstrom | A61F 5/566 128/859 |
| 2010/0154802 A1* | 6/2010 | Fuselier | A61F 5/566 128/848 |
| 2015/0216715 A1* | 8/2015 | Chung | A61F 5/566 128/848 |
| 2016/0022205 A1* | 1/2016 | Remmers | A61B 5/7264 600/301 |
| 2017/0106267 A1* | 4/2017 | Garner | A61M 16/0493 |
| 2018/0235824 A1* | 8/2018 | Nordgren | A61G 13/121 |
| 2018/0368952 A1* | 12/2018 | Chou | A61C 19/05 |
| 2019/0201226 A1* | 7/2019 | Bauerfeind | A61F 5/0102 |

\* cited by examiner

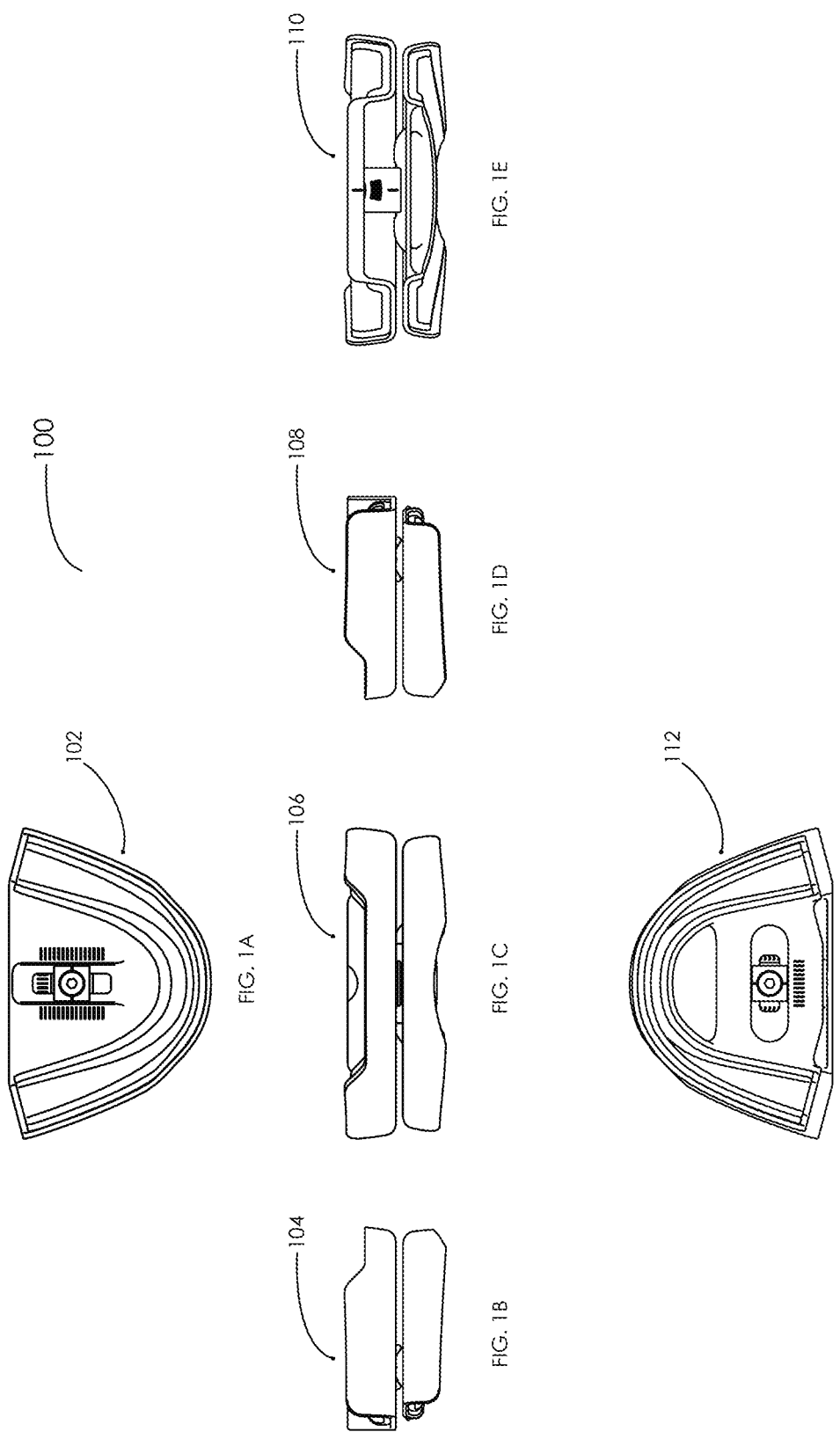

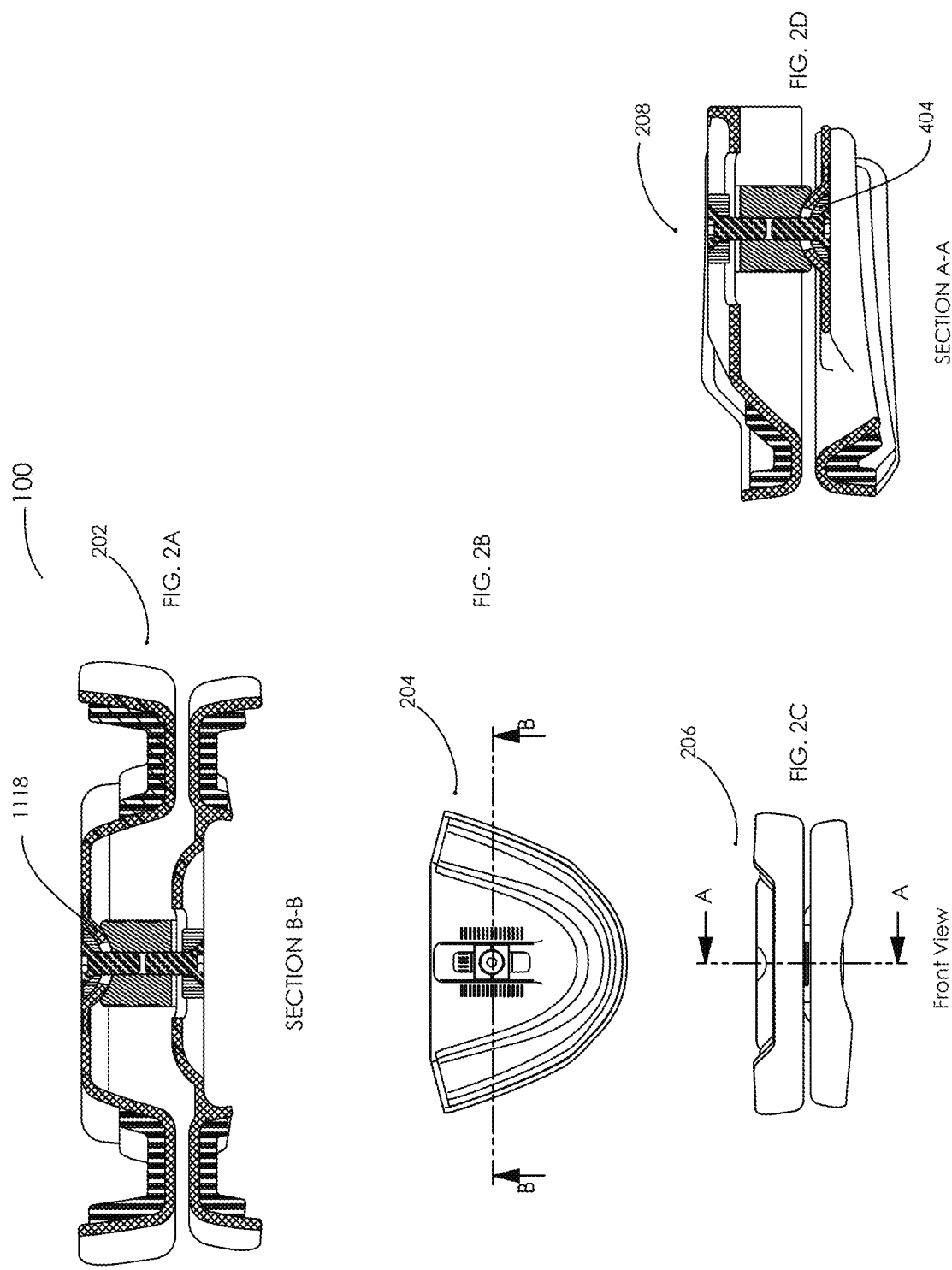

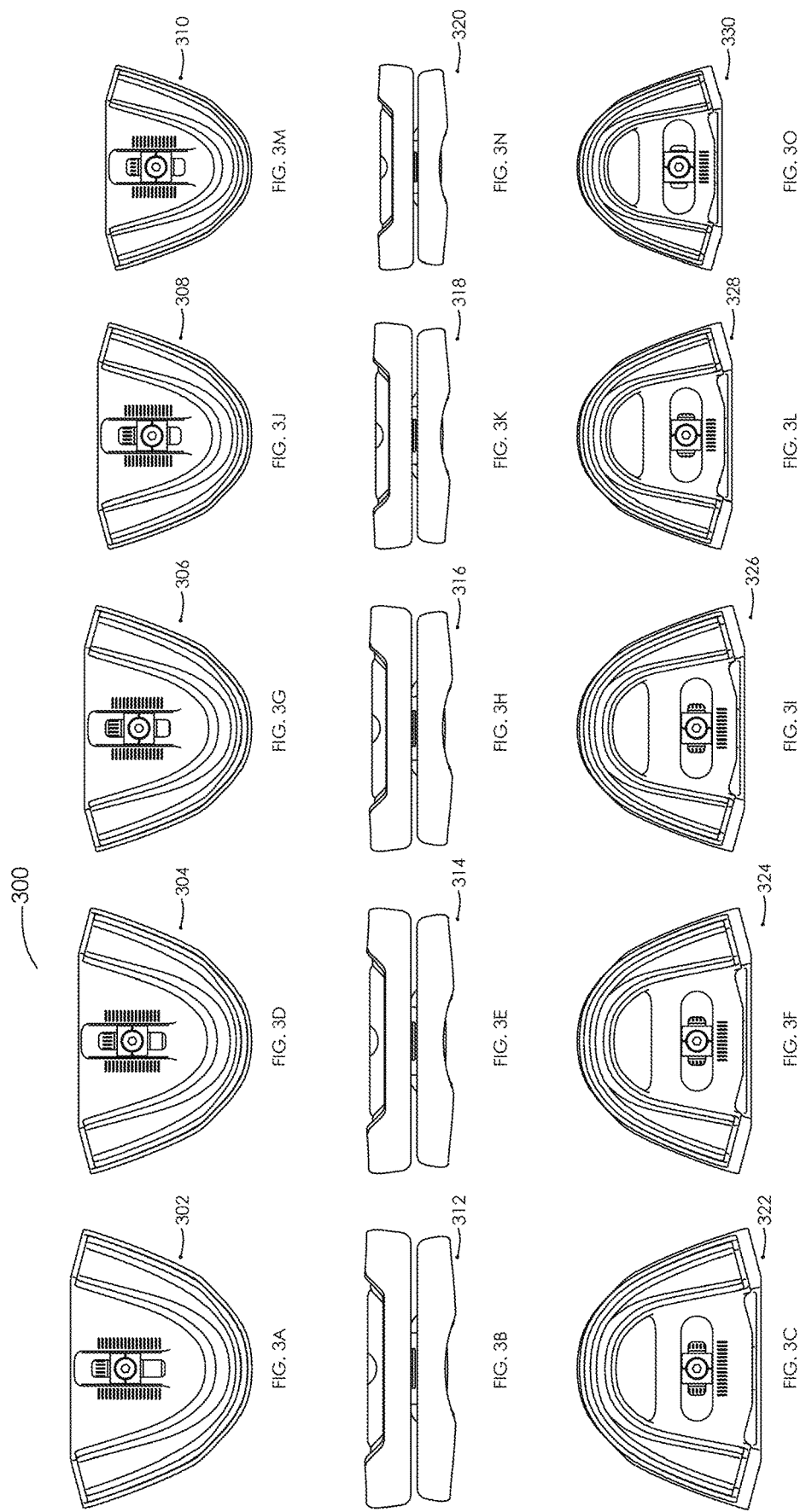

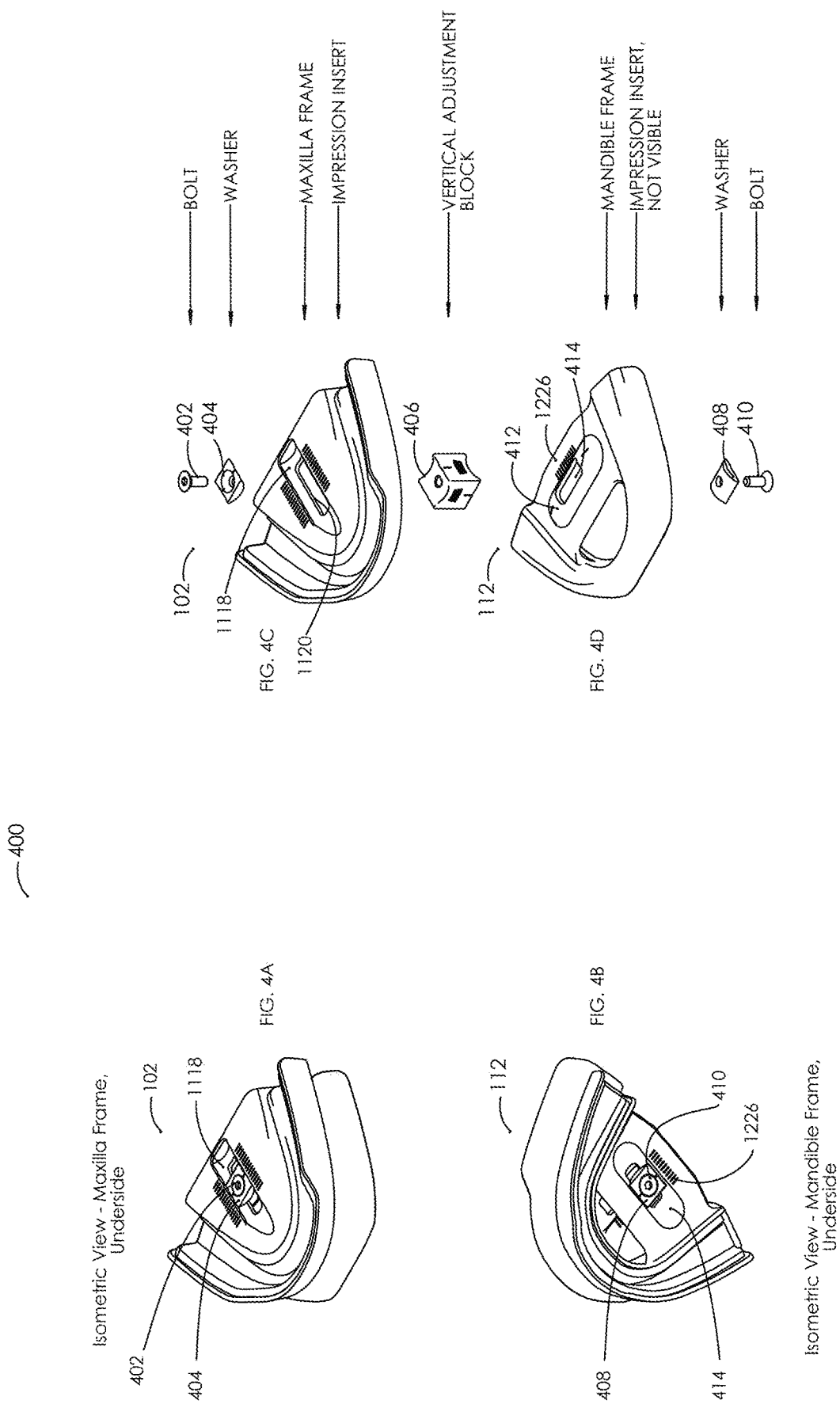

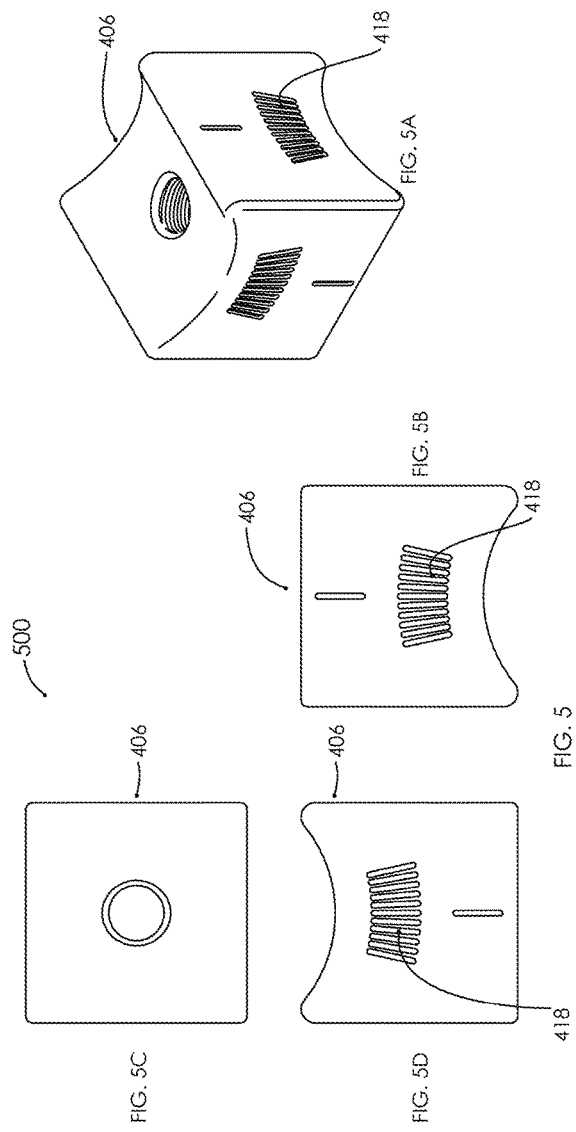
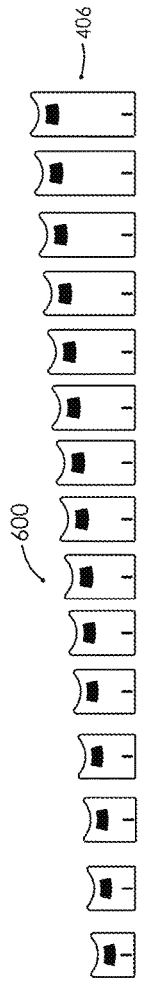
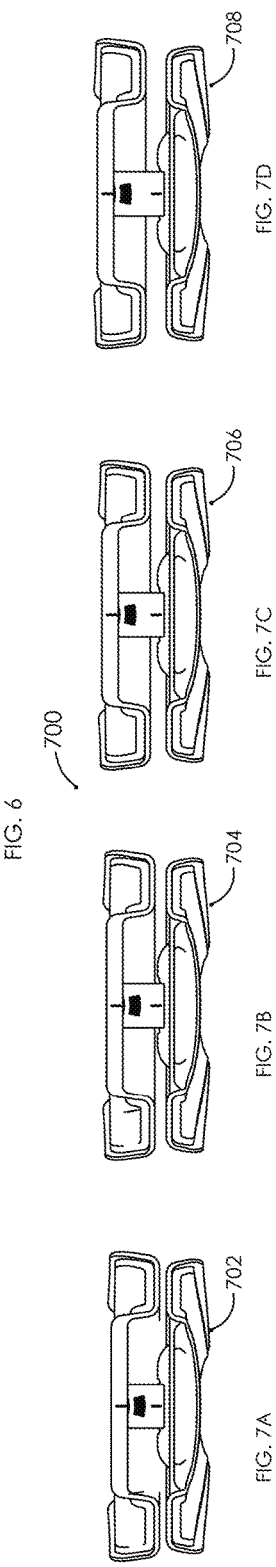

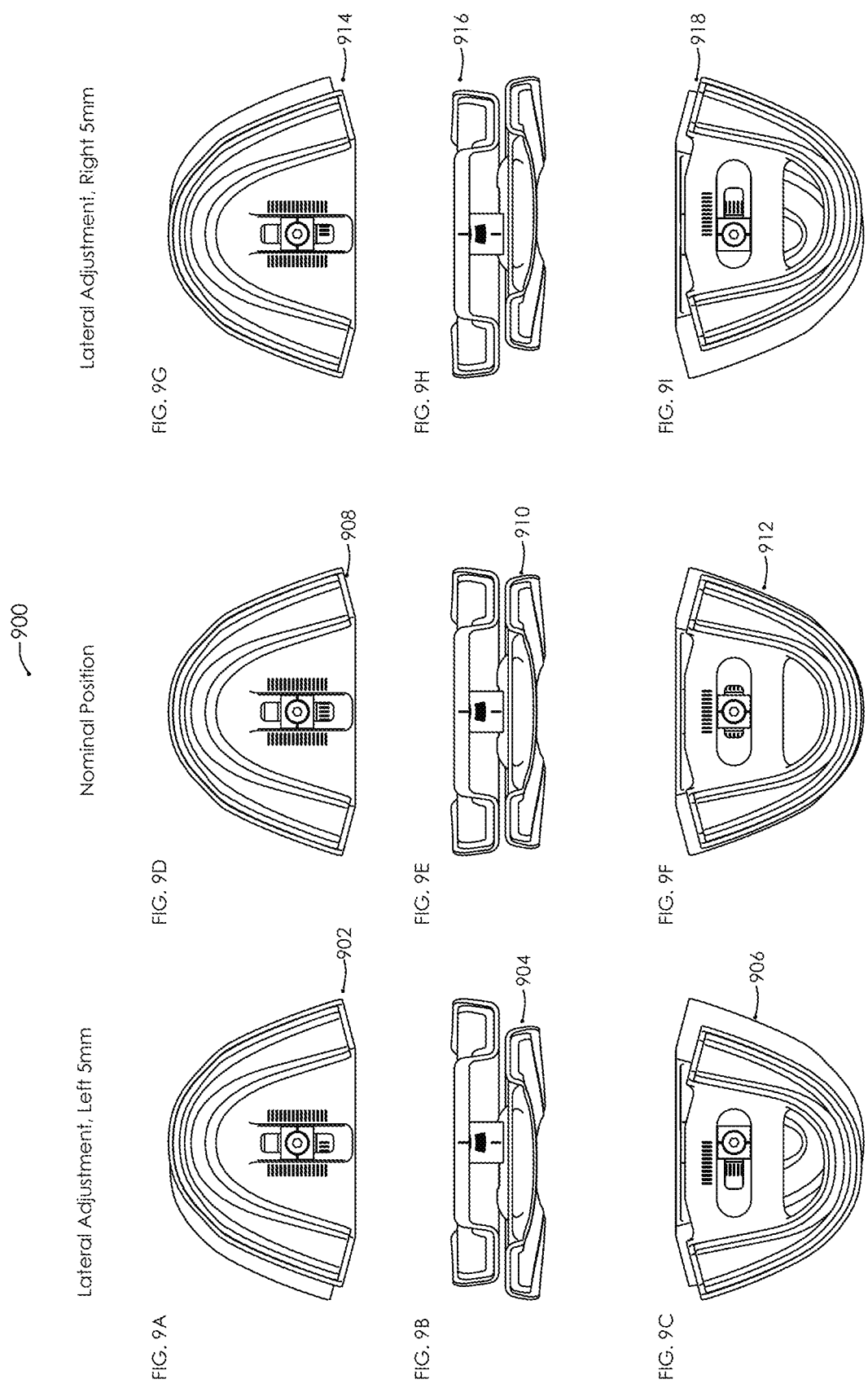

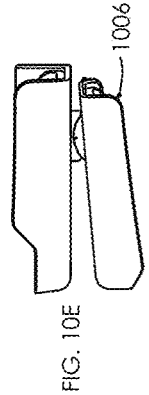
Nominal End-to-End Position
• 5 degrees of Pitch Down
• +1mm Vertical Adjustment Block
FIG. 10E

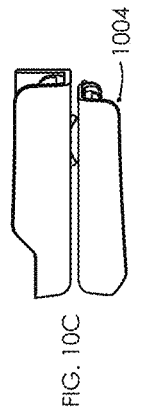
Nominal End-to-End Position
FIG. 10C

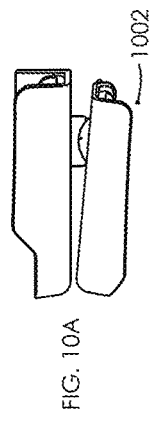
Nominal End-to-End Position
• 5 degrees of Pitch Up
• +2mm Vertical Adjustment Block
FIG. 10A

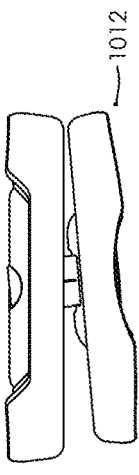
Nominal End-to-End Position
• 5 degrees left Roll
• +2mm Vertical Adjustment Block
FIG. 10F

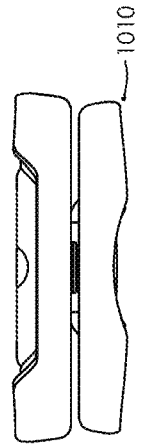
Nominal End-to-End Position
FIG. 10D

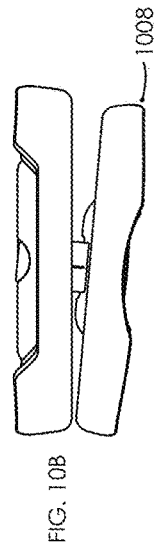
Nominal End-to-End Position
• 5 degrees right Roll
• +2mm Vertical Adjustment Block
FIG. 10B

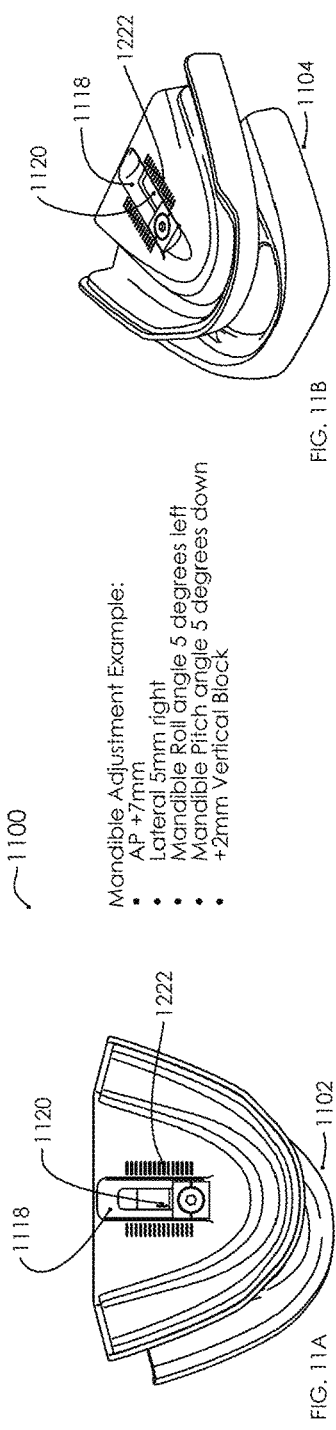
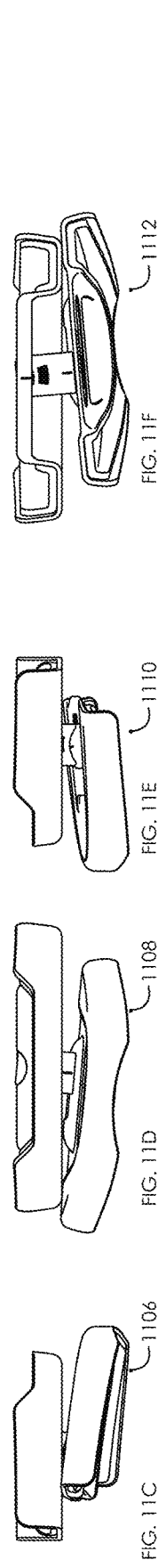
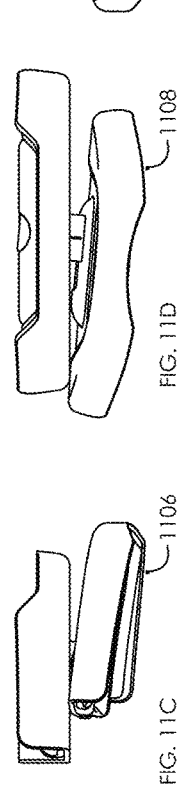
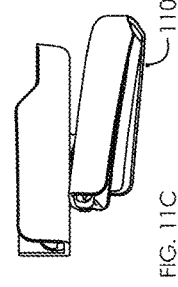
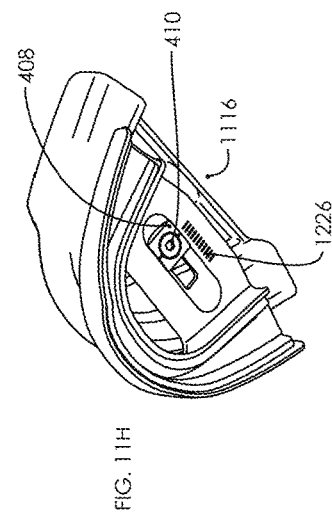
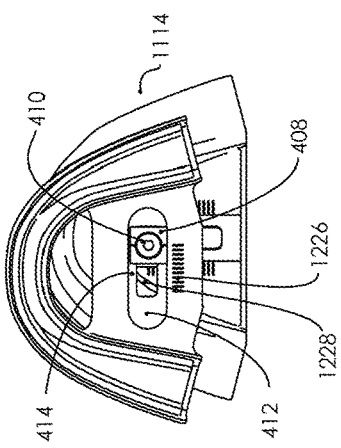
Mandible Adjustment Example:
- AP +7mm
- Lateral 5mm right
- Mandible Roll angle 5 degrees left
- Mandible Pitch angle 5 degrees down
- +2mm Vertical Block
FIG. 11A  FIG. 11B  FIG. 11C  FIG. 11D  FIG. 11E  FIG. 11F  FIG. 11G  FIG. 11H

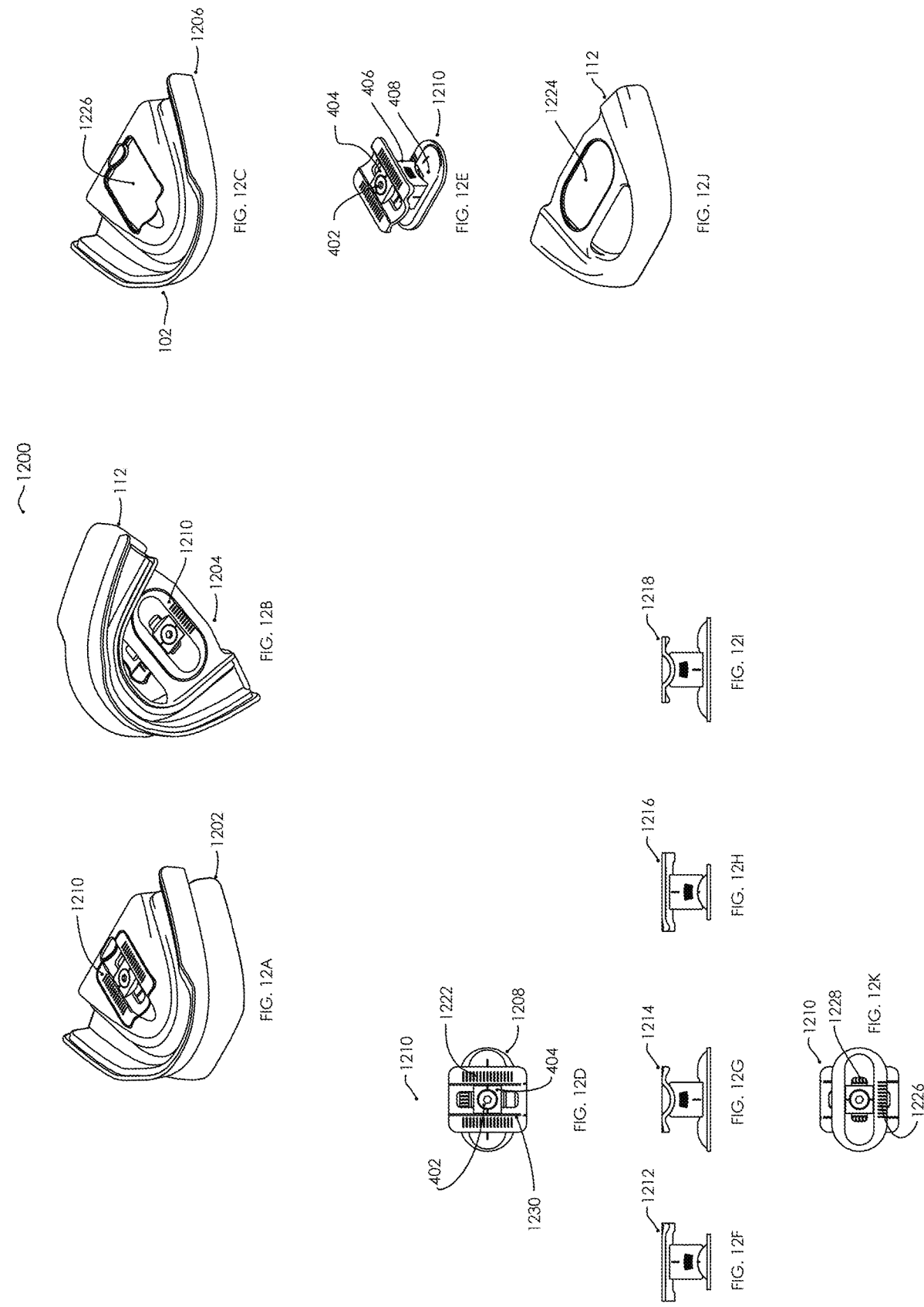

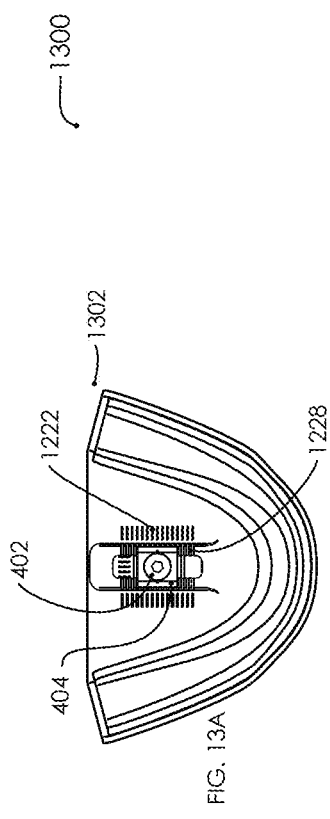
FIG. 13A
FIG. 13B
FIG. 13C
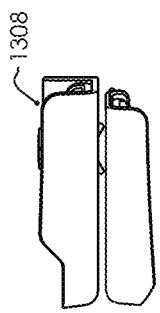
FIG. 13D
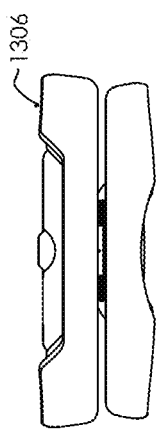
FIG. 13E
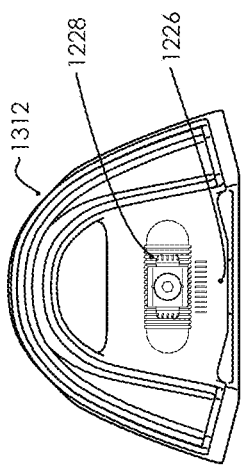
FIG. 13F

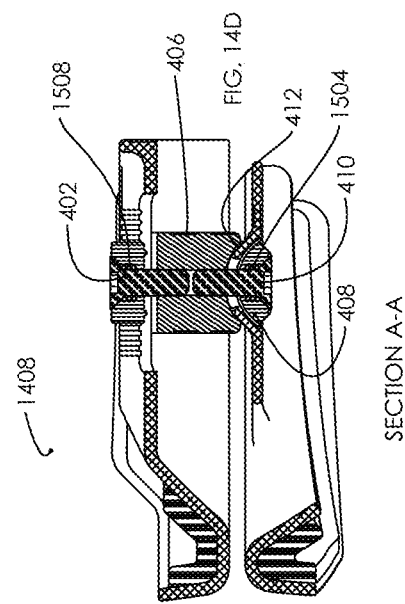
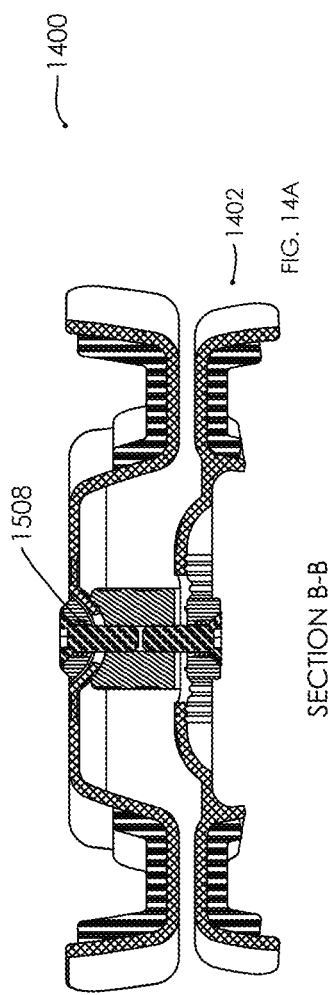
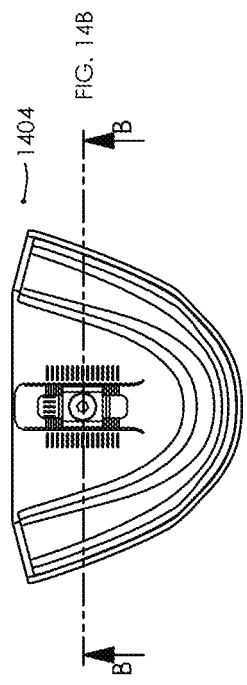
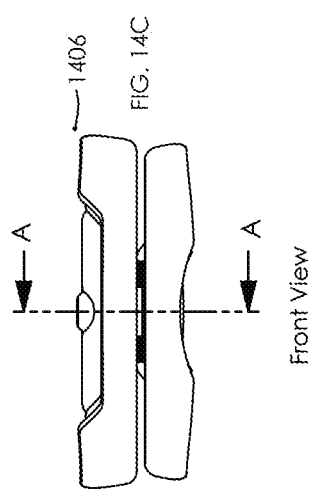

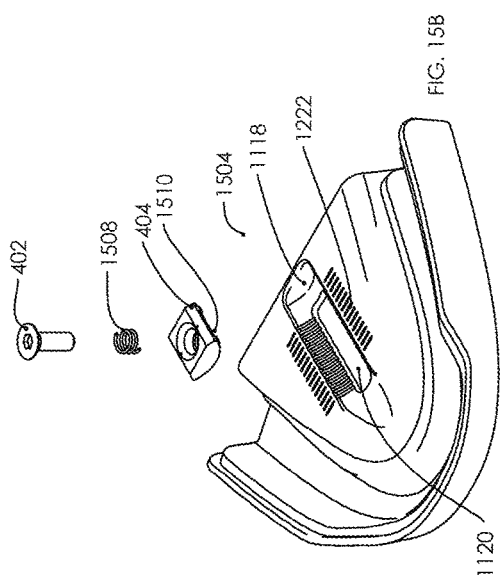
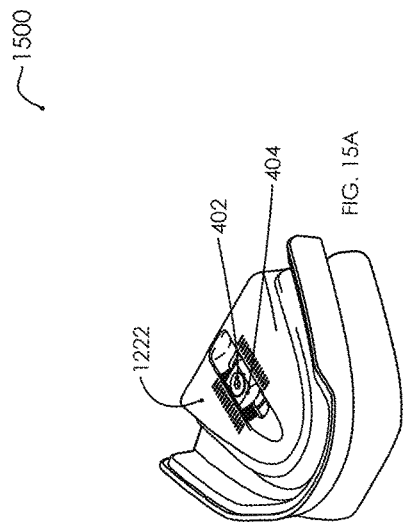
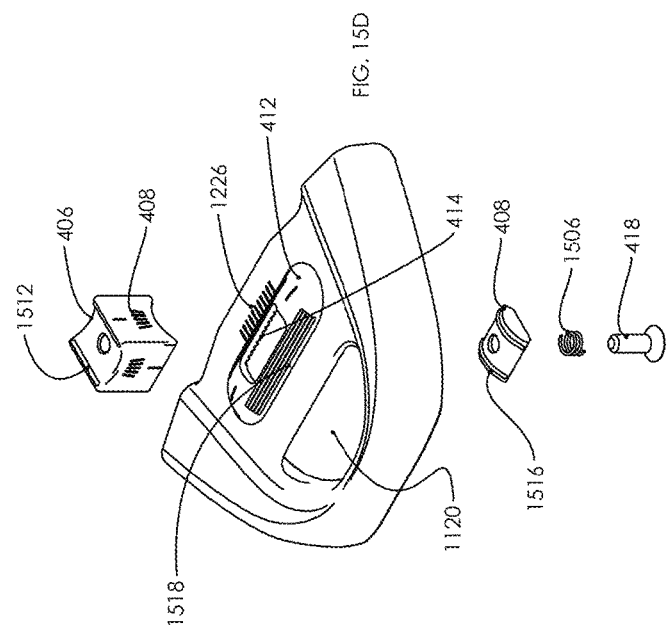

THERAPEUTIC POSITION VERIFYING TOOL FOR ORAL APPLIANCES

CROSS-REFERENCE TO RELATED APPLICATION

This application claims benefit of U.S. provisional patent application Ser. No. 62/737,696, filed Sep. 27, 2018, the entirety of which is incorporated herein by this reference thereto.

BACKGROUND

Technical Field

The present disclosure relates generally to fitting of oral appliances. More particularly, the present disclosure relates to a therapeutic position verifying tool for oral appliances.

BACKGROUND IN FORMATION

According to the American Sleep Apnea Association, as many as 22 million Americans may suffer from sleep apnea. Up to 80% of the moderate and severe cases may be undiagnosed. The standard of care with moderate to severe sleep apnea is treatment with a CPAP (Continuous Positive Airway Pressure) machine. There are many problems with CPAP machines. Among them are: difficulty getting the right size and/or style of mask, trouble getting used to wearing the CPAP device, difficulty tolerating forced air, dry nose and/or mouth, feeling claustrophobic, mask leak, skin irritation or pressure sores, difficulty falling asleep, and so on. The difficulties inherent to CPAP machines lead to a high failure rate among patients using them—perhaps as much as 50%.

Oral appliances for sleep apnea are often used instead of CPAP. Additionally, a patient who has failed on CPAP may be a good candidate for oral appliance therapy. Some of the benefits of oral appliance therapy for sleep apnea may be:
- improved compliance compared to other treatments— notably CPAP;
- compact and portable;
- discreet—device is not visible to bed partner when mouth is closed; and
- immediate response—most patients see improvement on the first night.

The best candidates for oral appliance therapy for sleep apnea tend to be patients having mild-to-moderate obstructive sleep apnea, although patients who have failed on the CPAP machine may also be good candidates.

The current protocol and instrumentation used in dental sleep medicine have notable limitations in time efficiency, predictability, verification, and therapeutic outcome. Evidence-based science shows that every patient has a unique array of phenotypic characteristics, anatomy, and physiologic response to oral appliance therapy. As such, a target treatment position for an oral appliance for a patient is highly specific to the patient. Often, identifying the target treatment position for a given patient may require numerous rounds of titration and change in the oral appliance process.

Additionally, the response and verification process may be protracted due to administrative factors such as paperwork, dealing with third-party payers and back-and-forth communication between the various providers involved: the dentist who is producing the oral appliance, the board-certified sleep physician and the patient's primary care provider.

Several bite methods are taught in dental sleep medicine. Some involve relatively more instrumentation and may correlate to the patient's jaw joint and muscles of mastication, while others are much less complex, often being one-dimensional, generally in the anteroposterior plane of occlusion—such as the George Gauge. However, all bite methods for oral appliance therapy start position fall into one of two categories: Category 1: Dynamic or Complex Airway Bite and Category 2: Static Simplified Airway Bite. Below are some Category 1 Bite Methods:
- Pharyngometer Bite Using AIRWAY METRICS jigs (AIRWAY METRICS LLC, Seattle, WA);
- Neuromuscular MYOBITE Using K7 OCCLUSAL EVALUATION SYSTEM and myometer (MYOTRONICS-NOROMED, Kent WA)
- Neuromuscular MYOBITE using BioPaK (DIGITAL DENTAL, Paddington, AU) and MicroTens (TRUMEDIC, INC., Kings Park, NY);
- LVI Tag Bite (LAS VEGAS INSTITUTE, Las Vegas, NV; and
- Moses Bite System (ALAN MOSES, Indian Wells, CA).

Below are some Category 2 Bite Methods:
- George Gauge Bite (SOMNOMED, Plano, TX);
- Airway Metrics Jigs (bite only) (AIRWAY METRICS LLC, Seattle, WA;
- Phonetics Bite; and
- Swallow Bite.

Currently, there is a single instrumentation protocol used that considers the vertical dimension of occlusion (VDO) in addition to anteroposterior (AP) based on the use of a Pharyngometer and Airway Metrics jigs. There is a lack of evidence-based literature with this protocol, but anecdotal findings from thousands of dentists throughout North America show that minimum protrusion and fewer side effects are obtained when using the Pharyngometer to find a therapeutic bite position that considers the vertical dimension in addition to AP.

Unfortunately, this protocol calls for measurements (during modified Mueller's Collapse) done while the patient is awake and not sleeping. Even though the pharyngometer can measure a true cross-sectional area of the collapsibility of the patient's airway, wake-time measurements do not accurately represent the cross-sectional area of the airway during sleep.

Currently in the market is the MATRX SYSTEM (ZEPHYR SLEEP TECHNOLOGIES, Calgary, AB, Canada), which records oral appliance treatment position during an in-lab sleep test (Polysomnogram) and identifies the patient as a "responder" or "non-responder".

A release of the MATRX PLUS, which is the same version of MATRX except as a home sleep test system instead of an in-lab sleep test (PSG), is anticipated. However, both systems only measure the bite position in a single dimension, the Anteroposterior, only (AP). The vertical and lateral dimensions are completely neglected and are arbitrarily determined. Thus, there is no sensitivity for all "non-responders" as true "non-responders" because a vertical component may very well make them be responders. The second problem is that, of the responders, several of them require 70% to 100% of their maximum protrusion which can lead to more patient discomfort, more side effects, and negatively impact compliance. Furthermore, within the "responder" pool of patients, in order to classify the patient as a responder, there is often a need to protrude the patient's lower jaw to 90-100% of the patient's maximum threshold, causing pronounced soreness, discomfort and lack of compliance due to the side effects caused by the extreme protrusion of the lower jaw.

These side effects would be unnecessary if the patient can achieve the same "responder" response with less protrusion by taking other dimensions, such as vertical and lateral, into consideration.

SUMMARY

A therapeutic position verifying tool is a semi-custom oral appliance equipped with adjustment assemblies for setting trial occlusion dimensions during a process of fitting a patient for an oral appliance. The oral appliance is fabricated from a polymer such as control-cured PMMA. The adjustment assemblies enable the vertical, anterior-posterior and lateral occlusion dimensions to be set. Occlusion dimensions are measured directly with a pharyngometer or indirectly with a bite registration method. The measurements are transferred to the tool by setting the tool to the measured dimensions using the adjustment assembly. When a target therapeutic position for a patient is found, the patient tests the position during the night with a Polysomnogram (PSG) or Home Sleep Test (HST). The use of the tool in verifying a therapeutic position for an oral appliance eliminates much of the time-consuming process of titrating the appliance to the patient.

BRIEF DESCRIPTION OF THE DRAWINGS

FIG. 1A provides an orthographic view of a therapeutic position-verifying tool for oral appliances;

FIG. 1B provides an orthographic view of a therapeutic position-verifying tool for oral appliances;

FIG. 1C provides an orthographic view of a therapeutic position-verifying tool for oral appliances;

FIG. 1D provides an orthographic view of a therapeutic position-verifying tool for oral appliances;

FIG. 1E provides an orthographic view of a therapeutic position-verifying tool for oral appliances;

FIG. 1F provides an orthographic view of a therapeutic position-verifying tool for oral appliances;

FIG. 2A provides an orthographic section view of the therapeutic position-verifying tool of FIGS. 1A-1F;

FIG. 2B provides and orthographic section view of the therapeutic position-verifying tool of FIGS. 1A-1F;

FIG. 2C provides an orthographic section view of the therapeutic position-verifying tool of FIGS. 1A-1F;

FIG. 2D provides an orthographic section view of the therapeutic position-verifying tool of FIGS. 1A-1F;

FIG. 3A provides a plan view of the therapeutic position-verifying tool of FIGS. 1A-1F;

FIG. 3B provides a plan view of the therapeutic position-verifying tool of FIGS. 1A-1F;

FIG. 3C provides a plan view of the therapeutic position-verifying tool of FIGS. 1A-1F;

FIG. 3D provides a plan view of the therapeutic position-verifying tool of FIGS. 1A-1F;

FIG. 3E provides a plan view of the therapeutic position-verifying tool of FIGS. 1A-1F;

FIG. 3F provides a plan view of the therapeutic position-verifying tool of FIGS. 1A-1F;

FIG. 3G provides a plan view of the therapeutic position-verifying tool of FIGS. 1A-1F;

FIG. 3H provides a plan view of the therapeutic position-verifying tool of FIGS. 1A-1F;

FIG. 3I provides a plan view of the therapeutic position-verifying tool of FIGS. 1A-1F;

FIG. 3J provides a plan view of the therapeutic position-verifying tool of FIGS. 1A-1F;

FIG. 3K provides a plan view of the therapeutic position-verifying tool of FIGS. 1A-1F;

FIG. 3L provides a plan view of the therapeutic position-verifying tool of FIGS. 1A-1F;

FIG. 3M provides a plan view of the therapeutic position-verifying tool of FIGS. 1A-1F;

FIG. 3N provides a plan view of the therapeutic position-verifying tool of FIGS. 1A-1F;

FIG. 3O provides a plan view of the therapeutic position-verifying tool of FIGS. 1A-1F;

FIG. 4A provides an isometric view of the therapeutic position-verifying of FIGS. 1A-1F;

FIG. 4B provides an isometric view of the therapeutic position-verifying of FIGS. 1A-1F;

FIG. 4C provides an isometric view of the therapeutic position-verifying of FIGS. 1A-1F;

FIG. 4D provides an isometric view of the therapeutic position-verifying of FIGS. 1A-1F;

FIG. 5A shows a view of a vertical adjustment block in the therapeutic position-verifying tool of FIGS. 1A-1F;

FIG. 5B shows a view of a vertical adjustment block in the therapeutic position-verifying tool of FIGS. 1A-1F;

FIG. 5C shows a view of a vertical adjustment block in the therapeutic position-verifying tool of FIGS. 1A-1F;

FIG. 5D shows a view of a vertical adjustment block in the therapeutic position-verifying tool of FIGS. 1A-1F;

FIG. 6 shows a plurality of vertical adjustment blocks in a range of sizes;

FIG. 7A provides a view of the therapeutic position-verifying tool with various vertical adjustment blocks;

FIG. 7B provides a view of the therapeutic position-verifying tool with various vertical adjustment blocks;

FIG. 7C provides a view of the therapeutic position-verifying tool with various vertical adjustment blocks;

FIG. 7D provides a view of the therapeutic position-verifying tool with various vertical adjustment blocks;

FIG. 9A shows an orthographic view of the therapeutic position-verifying tool in a position of lateral adjustment;

FIG. 9B shows an orthographic view of the therapeutic position-verifying tool in a position of lateral adjustment;

FIG. 9C shows an orthographic view of the therapeutic position-verifying tool in a position of lateral adjustment;

FIG. 9D shows an orthographic view of the therapeutic position-verifying tool in a position of lateral adjustment;

FIG. 9E shows an orthographic view of the therapeutic position-verifying tool in a position of lateral adjustment;

FIG. 9F shows an orthographic view of the therapeutic position-verifying tool in a position of lateral adjustment;

FIG. 9G shows an orthographic view of the therapeutic position-verifying tool in a position of lateral adjustment;

FIG. 9H shows an orthographic view of the therapeutic position-verifying tool in different positions of lateral adjustment;

FIG. 9I shows an orthographic view of the therapeutic position-verifying tool in a position of lateral adjustment;

FIG. 10A shows an orthographic view of the therapeutic position-verifying tool in a position of pitch adjustment;

FIG. 10C shows an orthographic view of the therapeutic position-verifying tool in a position of pitch adjustment;

FIG. 10E shows an orthographic view of the therapeutic position-verifying tool in a position of pitch adjustment;

FIG. 10B shows an orthographic view of the therapeutic position-verifying tool in a position of roll adjustment;

FIG. 10D shows an orthographic view of the therapeutic position-verifying tool in a position of roll adjustment;

FIG. 10F shows an orthographic view of the therapeutic position-verifying tool in a position of roll adjustment;

FIG. 11A shows an orthographic view of the tool in a multi-adjustment example;

FIG. 11B shows an isometric view of the tool in a multi-adjustment example;

FIG. 11C. shows an orthographic view of the tool in a multi-adjustment example;

FIG. 11D. shows an orthographic view of the tool in a multi-adjustment example;

FIG. 11E. shows an orthographic view of the tool in a multi-adjustment example;

FIG. 11F. shows an orthographic view of the tool in a multi-adjustment example;

FIG. 11G. shows an orthographic view of the tool in a multi-adjustment example;

FIG. 11H. shows an isometric view of the tool in a multi-adjustment example;

FIGS. 12A-12K provide a plurality of orthographic and isometric views, wherein a sub-assembly of adjustment features been isolated from the assembly;

FIG. 12A provides an isometric view, wherein a sub-assembly of adjustment features has been isolated from the assembly;

FIG. 12B provides an isometric view, wherein a sub-assembly of adjustment features has been isolated from the assembly;

FIG. 12C provide an isometric view, wherein a sub-assembly of adjustment features has been isolated from the assembly;

FIG. 12D provides an orthographic view, wherein a sub-assembly of adjustment features has been isolated from the assembly;

FIG. 12E provides an isometric view, wherein a sub-assembly of adjustment features has been isolated from the assembly;

FIG. 12F provides an orthographic view, wherein a sub-assembly of adjustment features has been isolated from the assembly;

FIG. 12G provides an isometric view, wherein a sub-assembly of adjustment features has been isolated from the assembly;

FIG. 12H provides an orthographic view, wherein a sub-assembly of adjustment features has been isolated from the assembly;

FIG. 12I provides an orthographic view, wherein a sub-assembly of adjustment features has been isolated from the assembly;

FIG. 12J provides an isometric view, wherein a sub-assembly of adjustment features has been isolated from the assembly;

FIG. 12K provides an orthographic view, wherein a sub-assembly of adjustment features has been isolated from the assembly FIG. 13A provides an orthographic view of the tool showing additional flute features;

FIG. 13B provides an orthographic view of the tool showing additional flute features;

FIG. 13C provides an orthographic view of the tool showing additional flute features;

FIG. 13D provides an orthographic view of the tool showing additional flute features;

FIG. 13E provides an orthographic view of the tool showing additional flute features;

FIG. 13F provides an orthographic view of the tool showing additional flute features;

FIG. 14A provides an orthographic section view, wherein the fluted feature option is cut through the major planes of the assembly in an end-to-end position showing components in position, including springs;

FIG. 14B provides an orthographic section view, wherein the fluted feature option is cut through the major planes of the assembly in an end-to-end position showing components in position, including springs;

FIG. 14C provides an orthographic section view, wherein the fluted feature option is cut through the major planes of the assembly in an end-to-end position showing components in position, including springs;

FIG. 14D provides an orthographic section view, wherein the fluted feature option is cut through the major planes of the assembly in an end-to-end position showing components in position, including springs;

FIG. 15A provides and isometric view showing the tool in an assembled and end-to-end position with Fluted features. An exploded view shows all major components of the fluted feature option;

FIG. 15B provides an isometric view showing the tool in an assembled and end-to-end position with Fluted features. An exploded view; shows all major components of the fluted feature option;

FIG. 15C provides an isometric view showing the tool in an assembled and end-to-end position with Fluted features. An exploded view shows all major components of the fluted feature option; and FIG. 15D provides and isometric view showing the tool in an assembled and end-to-end position with Fluted features. An exploded view shows all major components of the fluted feature option.

DETAILED DESCRIPTION

Figure 8A:
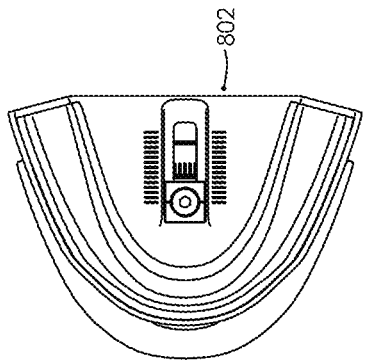
FIG. 8A shows an orthographic view of the therapeutic position-verifying tool in a position of anterior-posterior (AP) adjustment.

A therapeutic position verifying tool is a semi-custom oral appliance equipped with adjustment assemblies for setting trial occlusion dimensions during a process of fitting a patient for an oral appliance. The oral appliance is fabricated from a polymer such as control-cured PMMA. The adjustment assemblies enable the vertical, anterior-posterior, pitch, roll and lateral occlusion dimensions to be set. Occlusion dimensions are measured directly with a pharyngometer or indirectly with a bite registration method. The measurements are transferred to the tool by setting the tool to the measured dimensions using the adjustment assembly. When a target therapeutic position for a patient is found, the patient tests the position during the night with a Polysomnogram (PSG) or Home Sleep Test (HST). The use of the tool in verifying a therapeutic position for an oral appliance eliminates much of the time-consuming process of titrating the appliance to the patient.

The therapeutic position verifying tool is compatible with all airway approaches to bite registration. Whatever approach the dentist employs in determining bite position, the dimensions of bite position can be transferred to the therapeutic position-verifying tool. Calipers can be used to measure vertical, AP and lateral dimensions occlusion shown by a bite impression and these measurements can be transferred precisely to the therapeutic position verifying tool.

The therapeutic position verifying tool is for use in the verification, testing and treatment of obstructive sleep apnea by a clinician. The tool is a semi-permanent device with which the clinician may adjust the position of the lower jaw or mandible accurately and incrementally to improve symptoms of obstructive sleep apnea, after which a patient may choose to use a permanent oral appliance that references a molded impression of their bite and is then fabricated by an oral appliance supplier.

Because human anatomy and physiology is complex and highly individual, an approach to determining the target therapeutic position should have the following goals:

The least amount of change m both mandibular protrusion and vertical occlusion while making the most beneficial gain in lowering RDI/REI (Respiratory Disturbance Index/Respiratory Event Index) or AHI (Apnea/Hypopnea) Index;

The target bite must be sensitive to the 3 dimensions of a patient's bite/occlusion and occlusion trajectory, which are vertical, AP (anteroposterior) and lateral, plus one or more of the angles of rotation about the axes of these dimensions: pitch, roll and yaw.

The therapeutic position for an oral appliance is a prescription based on the patient's specific phenotype, medical history, physiology and other significant factors. Thus, verification of the therapeutic position for an oral appliance using the tool is an analogous process to dose titration or calibration in medicine.

The current protocol established by the American Academy of Sleep Medicine and the American Academy of Dental Sleep Medicine states that dentists may screen for airway issues and sleep disorder breathing, but the official diagnosis of obstructive sleep apnea in any threshold is only to be done by a board-certified sleep physician/MD. After such diagnosis, the primary care physician or the sleep MD may elect to prescribe oral appliance therapy for mild and moderate sleep apnea cases and those severe cases who fail CPAP, or who are CPAP intolerant after the Sleep MD has done a trial with CPAP.

Home sleep tests have become relatively standard in recent years, supported by the medical insurance industry as well as many sleep MDs. Nonetheless, Polysomnography (PSG), a test used to diagnose sleep disorders, remains the gold standard in sleep medicine. Thus, when patients have parasomnias, such as sleep walking or night terrors, other sleep issues such as restless leg syndrome, narcolepsy, insomnia, and so on, PSG's are deemed as essential diagnostic tool. When patients are screened for sleep breathing disorder such as obstructive sleep apnea (OSA) in a dental office, the Home Sleep Test (HST) is most often used, while a board-certified Sleep MD does the official interpretation of the HST and makes the diagnosis of OSA, if appropriate.

It should be noted that if the home sleep test is done only for screening purposes and not for diagnosis, the dentist needs to follow proper patient consent procedure and must still follow through normal protocol and diagnostic channels if there are findings suggestive of OSA. Thus, the dentist is required to involve the sleep MD before any oral appliance may be considered.

The current protocol for dentists for screening patients in the dental office involves the following:
1) Patient shows signs/symptoms, and other early indicators of pathology during dental exam;
2) Patient may have preliminary screening for airway issues on a pharyngometer or rhinometer;
3) A physician orders a home sleep test for the patient;
4) Patient waits for the board-Certified Sleep MD to make official diagnosis and then determine whether oral appliance therapy is an option or CPAP;
5) Patient, if prescribed oral appliance therapy, goes back to the dental office for more dental records and bite impression method for determining oral appliance therapy starting position. The starting position is, more often than not, an estimation, involving a fair degree of guesswork, for the target position which will eventually come from titration of the oral appliance;
6) Patient waits for the lab to make and return the oral appliance for fitting;
7) Patient will have comfort, compliance, potential side effects addressed and titration will be needed;
8) Patient then will need to show efficacy of the oral appliance in the target position with another home sleep test and then must wait for the Sleep MD to evaluate and return a final recommendation; and
9) Patient is then put on follow up visits IF and only IF that position of the oral appliance is deemed a successful response to oral appliance therapy by the sleep MD.

The pharyngometer bite registration method with airway metrics jigs allows the provider to evaluate a vertical position, but it is performed while the patient is awake and sitting upright. However, during sleep, with the patient reclining in a supine position, there is a high probability that collapse and airway issues are aggravated over those in awake times and in an upright position, especially when comparing REM-stage (Rapid Eye Movement) sleep to wake times. Also, the pharyngometer bite position still suffers the drawback that it is a wake-time measurement, with final verification not being possible until sleep test results with the oral appliance in user come back. The primary benefit, then, from using the pharyngometer is that a vertical dimension is taken into account, and thus less titration is needed and far less guess work is needed for identifying a target therapeutic position.

Turning now to the drawings, FIGS. 1A-1F provide orthographic views of a therapeutic position-verifying tool 100 for oral appliances in an end-to-end position, also known as a nominal starting position, in which the ends of each frame, when positioned in a patient's mouth, are co-linear with each other. It will be appreciated that the end-to-end position is merely a starting position because few patients being evaluated for obstructive sleep disorders are likely to have static occlusion in which the maxillary teeth and the mandibular teeth are in perfect alignment. Embodiments of the tool may include two frames, a maxilla frame 102 for the upper jaw and a mandible frame 112 for the lower jaw.

FIG. 1A provides a top plan view of the maxilla frame 102, while FIG. 1F provides a bottom plan view of the mandible frame 112. FIG. 1B provides a right side elevation 104 of the tool. FIG. 1C provides a front elevation 106 of the tool, while FIG. 1D provides a left side elevation 108. Finally, FIG. 1E provides a rear elevation 110.

As FIGS. 1B-1E show, the frames 102, 112 during use, are placed in the patient's mouth, over their teeth, so that impressions can be made. In embodiments, each frame is pre-filled impression material, which allows an impression of the patient's teeth to be made by having the patient bite down while the tool, with the impression material is positioned inside the patient's mouth. The impression material may also assist retention of the tool in the desired position.

In embodiments, the mandible frame 112 is positioned or adjusted in relation to the maxilla frame 102. Adjustment of the position of the mandible allows obstruction(s) to the patient's airway to be reduced so that flow of air across the airway is improved. A range of adjustments is made possible through the interaction and secure connection of the Mandible Frame 112 to the Maxilla Frame 102 by means of a vertical adjustment block 406. Using the tool, adjustments may be made to a large number of occlusion parameters:

Anterior-posterior (AP) in millimeters;
Lateral in millimeters;
Vertical in millimeters;
Roll in angular degrees; and
Pitch in angular degrees.

It is to be appreciated that "roll," "pitch" and "yaw" constitute rotational descriptors. If the AP, lateral and vertical dimensions of occlusion are seen as axes, roll, pitch and yaw may be seen as rotation about the axes, with yaw constituting rotation about the vertical axis, pitch constituting rotation about the lateral axis and roll constituting rotation about the AP axis.

Both the mandible 112 and maxilla Frames 102 have gutters 404, 1118 between the arch of the teeth within the oral cavity of the patient. Each gutter has both convex and concave sides. The concave side of the gutter 1118 on the Maxilla Frame 102 faces up and is aligned with the patient's AP axis. At the base of the gutter 1118 is an open slot 1120 to allow assembly of a bolt 402, 404 component. The concave side of the gutter 404 in the mandible frame 112 faces down and is aligned with the patient's lateral axis. At the base of the gutter is an open slot 414 to allow assembly of a bolt component 408, 410. As shown herein below, vertical adjustment blocks 406 also have gutters at both end of each adjustment block that correspond to those on the frames. As shown in FIG. 4, the axes of the gutters on the vertical adjustment blocks are perpendicular to the corresponding frame gutter.

FIGS. 2A-2D provide orthographic section views of the therapeutic position-verifying tool 100 of FIGS. 1A-1F. Two cross-section views show the tool cut through the major planes of the assembly in the end-to-end position.

Section B-B 204 (FIGS. 2A, 2B) shows the tool cut through horizontally 202 at the approximate center of the tool. Section B-B clearly shows the maxillary gutter 1118.

Section A-A 206 (FIGS. 2C, 2D) shows the tool 100 cut through vertically 208 along the center line. The mandibular gutter 404 is clearly visible.

FIGS. 3A-3O provide orthographic views 300 of the therapeutic position-verifying tool 100 of FIGS. 1A-1F showing various frame sizes available, from extra-large to extra-small. FIGS. 3A-3C provide top plan view 302, front elevation 312 and bottom plan view 322 of an extra-large tool 100. FIGS. 3M-3O provide top plan view 310, front elevation 320 and bottom plan view 330 of an extra-small tool 100. The remainder, FIGS. 3D-3L provide corresponding views 304-308, 314-318, 324-328 of a plurality of intermediate sizes.

FIGS. 4A-4B provide isometric views of the therapeutic position-verifying tool of FIGS. 1A-1F showing the tool in an assembled and end-to-end position. Exploded views (FIGS. 4C-4D) show the major components of the tool. Washer components 404, 408 rest within the open side of the gutters 1120, 412 on the maxilla 102 and mandible 112 frames, the washers 404, 408 allow alignment of bolts 402, 410 to secure the frames 102, 112 to the vertical adjustment block(s) 406 through the open slot in the base of each gutter.

As shown in FIGS. 4A and 4C, the maxilla frame 102 contains a gutter 1118 at the bottom of which is found an open slot 1120 to allow assembly of a bolt component 402, 404.

The use of the bolt 402 and washer 404 that are positioned in the maxilla gutter 1120 allow for AP and Roll adjustment. Tightening the bolt in the maxilla gutter 1120 secures the washer 404 in the concave gutter 1120 of the maxilla frame 102 and secures the underside of the maxilla gutter 1120 to the top gutter of the Vertical Adjustment Block 406. Loosening the bolt 402 in the maxilla gutter 1120 allows the vertical adjustment block 406 and the mandible frame 112 attached below to be moved and adjusted along the AP axis in mm and/or about the AP axis to provide Roll angle adjustment in degrees. The maxilla bolt 402 can then be tightened to secure the vertical adjustment block 406 and mandible frame 112 to the maxilla frame 102. Measuring increments 1222 of 1 mm are alongside of the maxilla gutter 1118 to provide verification of the adjustment amount. Angle increments 418 are on the sides of the vertical adjustment block 406 to verify the amount of Roll adjustment.

The use of the bolt 410 and washer 408 that are positioned in the mandible gutter slot 414 allow for lateral and pitch adjustment. Tightening the bolt 410 in the mandible gutter 414 secures the washer 408 into the open side of the gutter 414 of the mandible frame 112 and secures the convex side of the mandible gutter 414 to the lower concave gutter of the vertical adjustment block 406. Loosening the bolt 410 in the mandible gutter 414 allows the vertical adjustment block 406 and the maxilla frame 102 attached above to be moved and adjusted along the lateral axis in mm and/or about the lateral axis to provide pitch angle adjustment in degrees. The mandible bolt 410 can then be tightened to secure the vertical adjustment block 406 and the maxilla frame 102 to the Mandible Frame 112. Measuring increments 1226 of 1 mm are alongside of the mandible gutter 414 to provide verification of the adjustment amount. Angle increments 418 are on the sides of the Vertical Adjustment Block to verify the amount of pitch adjustment.

FIGS. 5A-5D show several views of a vertical adjustment block in the therapeutic position-verifying tool of FIGS. 1A-1F.

FIG. 6 shows a plurality of vertical adjustment blocks in a range of sizes from 0 mm (starting position) through to +14 mm of vertical adjustment. Vertical adjustment is provided in the tool by using interchangeable vertical Adjustment Blocks 600.

The distance between the position of the perpendicular gutters 1118, 404 may be increased by 1 mm by replacing a vertical adjustment block 406 of a first size with a vertical adjustment block 406 that is one size up. This allows for the mounting distance between the maxilla and mandible frames 102, 112 to increase as required, and also to maintain the AP and Roll as well as the Lateral and Pitch adjustability.

The starting vertical adjustment block 406, 0 mm, has a built-in starting position that pre-sets an end-to-end distance between the maxilla 102 and mandible frames 112 that allows for manufacture of a permanent oral appliance that is used for permanent treatment of obstructive sleep apnea. Although further adjustment in the AP and lateral axes and, in particular, in the Pitch and Roll Angles may complicate determination of oral appliance fabrication parameters, clinicians should always pay close attention to the distance between the maxilla 102 and mandible 112 frames to ensure that a permanent oral appliance will be feasible in relation to the adjustment position of the tool 100.

FIGS. 7A-7d provide a plurality 700 of views 702-708 of the tool 100 equipped with vertical adjustment blocks 406 in various sizes.

Figure 8B:
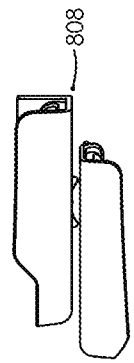
FIG. 8B shows an orthographic view of the therapeutic position-verifying tool in a position of anterior-posterior (AP) adjustment.
Figure 8C:
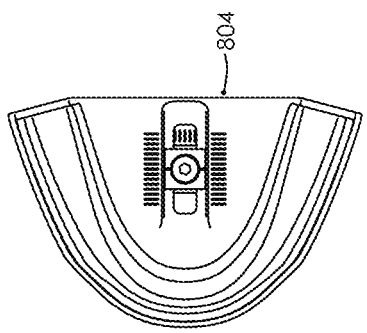
FIG. 8C shows an orthographic view of the therapeutic position-verifying tool in a position of anterior-posterior (AP) adjustment.
Figure 8D:
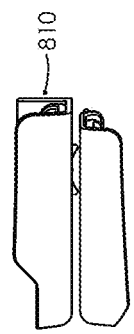
FIG. 8D shows an orthographic view of the therapeutic position-verifying tool in a position of anterior-posterior (AP) adjustment.
Figure 8E:
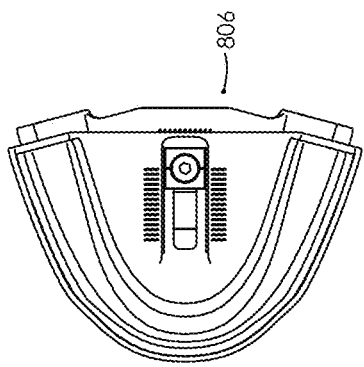
FIG. 8E shows an orthographic view of the therapeutic position-verifying tool in a position of anterior-posterior (AP) adjustment.
Figure 8F:
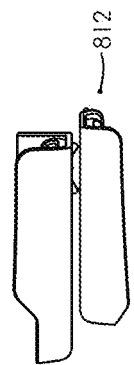
FIG. 8F shows an orthographic view of the therapeutic position-verifying tool in a position of anterior-posterior (AP) adjustment.

FIGS. 8A-8F show orthographic views 802-812 of the therapeutic position-verifying tool in different positions of anterior-posterior (AP) adjustment. The tool is shown in 3 different positions of AP adjustment. FIGS. 8C and 8D show the end-to-end position 804, 810. FIGS. 8A and 8B show +7 mm of mandible adjustment 802, 808 and FIGS. 8E and 8F show −7 mm of mandible adjustment 806, 812.

FIGS. 9A-9I show a plurality 900 of orthographic views 902-918 of the therapeutic position-verifying tool in 3 different positions of lateral adjustment. FIGS. 9D to 9F show end-to-end position, or no lateral adjustment. FIGS. 9A-9C show 5 mm of lateral adjustment to the patient's left and FIGS. 9G-9I show 5 mm of lateral adjustment to the patient's right FIGS. 10A, 10C and 10E show orthographic views 1002-1006 of the tool in different positions of pitch adjustment. The tool is shown in 3 views on the top of the page with a range of pitch adjustment. FIG. 10C shows no pitch adjustment. FIG. 10A shows 5 degrees of pitch adjustment upward to the Mandible Frame with +2 mm of vertical adjustment. FIG. 10E shows 5 degrees of pitch adjustment of the Mandible Frame downward with +1 mm of vertical adjustment.

FIGS. 10B, 10D and 10F 1008-1012 show the tool 100 with various roll adjustments. FIG. 10D shows no roll. FIG. 10B shows 5 degrees of roll adjustment to the Mandible Frame to the right of the patient, with +2 mm of vertical adjustment. FIG. 10F shows 5 degrees of roll adjustment to the Mandible Frame to the left of the patient, with +2 mm of vertical adjustment.

FIGS. 11A-11H 1102-1116 show orthographic and isometric views of the tool in a multi-adjustment example. FIGS. 11A and 11C-11G provide 6 orthographic views in a multi-adjustment example:

Anterior adjustment of the Mandible Frame by +7 mm;
lateral adjustment 5 mm to the right;
mandible roll 5 degrees to the left; and
mandible pitch 5 degrees down; and
+2 mm vertical adjustment.

FIGS. 11B and 11H provide isometric views showing the tool in the multi-adjusted positions described with respect to FIGS. 11A and 11C-1G.

The previously described embodiment of the tool with the adjustment features includes the frame arch integrated into a frame part. This frame is well-suited to a manufacturing process such as plastic injection molding, where suitable materials allow for accurate reproduction of the detail and features required for the various range of sizes required to suit the many different arch types and sizes of the human jaw. Each frame would incorporate a gutter, open slot and increments. The larger arched frames would allow for greater range of AP and Lateral adjustment i.e. a longer gutter and slot. The smaller arched frames would have reduced range of adjustment i.e. a shorter gutter and slot (see FIG. 3.) In embodiments, the range of pitch and roll adjustment may also be affected.

FIGS. 12A-K provide views 1202-1224 of an alternative embodiment of the tool 100 that includes the adjustment features as described above. However, in the alternative embodiment, the gutter and slot features, washers, bolts and connecting vertical adjustment block 406 have been isolated as a discrete sub-assembly 1210.

FIGS. 12A and 12B provide views 1202, 1204 of embodiments of the tool that includes the sub-assembly 1210. FIG. 12A provides a view of the maxilla frame with sub-assembly 1210 installed, while FIG. 12B provides a view of the mandible frame with the sub-assembly 1210 installed.

In embodiments, the sub-assembly 1210 may be made from suitable materials such as stainless steel. In embodiments, the sub-Assembly 1210 securely attaches to simplified maxilla and mandible frames through various means, for example either by mechanically interlocking or by being bonded in a molding process such as insert over-molding. The separation of the adjustment features in a sub-assembly 1210 allows for the optimization of the precise adjustment parts and the mass production of various-sized simplified frame arch parts. For example, a tool with stainless-steel adjustment sub-assembly may be pre-fitted at the point of manufacture or at the clinic as required by the clinician. This versatility may provide functional and or production benefits which may result in significant cost savings when compared to an integrated injection-moulded embodiment.

FIGS. 12C, 12E and 12J provide isometric views which together provide an exploded view of a tool 100 incorporating a discrete sub-assembly 1210. As shown in FIG. 12C, the maxilla frame 102 includes an opening 1226 into which the assembly 1210 (FIG. 12E) is received. Additionally, FIG. 12J shows the mandible frame 112 with an opening 1224 into which the assembly is received.

FIGS. 12D, 12F-12I and 12K together provide six orthographic views of the assembly 1210. FIG. 12D provides a top plan view while FIG. 12K provides a bottom plan view. FIGS. 12F-12I provide front, rear, left and right elevations.

FIGS. 13A-F show a plurality 1302-1312 of orthographic views of the tool 100 with additional flute features within concentrically curved surfaces of the frames and the vertical adjustment blocks. The sets of flute features on the top side and underside of the frames are perpendicular to each other. Fine flutes 1228 on the concave surface of the gutter of both frames, provide more control to the Doctor when making the fine adjustments to the position of the mandible frame 112 in relation to the maxilla frame 104. These flutes create a curved corrugated surface. The flutes 1228 are aligned perpendicular to the axis of the gutter. The washer 404, 408 that rests within the concave surface of the gutter 1120, 414 has two or more corresponding arc ribs 1510, 1516 that protrude from its convex surface and rest within the flutes 1228 of the gutter. Alignment of the curved ribs and flutes prevents the movement of the frame in relation to the washer and subsequent sub-assembly 1210 of bolt 402 and vertical adjustment block 406. The sets of flute features on the top side and underside of the frames are perpendicular to each other.

FIGS. 14A-14D provide orthographic sections views showing a therapeutic verifying tool fluted feature option cut through the major planes of the assembly in an end-to-end position showing components in position including springs 1508, 1506.

On the underside of the gutter on the convex gutter surface 412 are straight flute features 1518 (FIGS. 15A-D) that create a corrugated surface. These flute features run along the axis of the gutter on either side of the open slot of the gutter. The corresponding gutter surface on the vertical adjustment block has two straight ribs 1512 positioned on the outer edge of this concave gutter. The alignment of the flutes on the convex side of the frame gutter and the ribs on the concave gutter of the vertical adjustment block restricts angular adjustment about the axis of the gutter, whether this is the mandible frame 112 or the maxilla frame 102 rotating about the vertical adjustment block 406.

When the bolts 402, 418 are tightened, and the assembly is pulled together, the flutes restrict any adjustment or slipping. When a bolt is slightly loosened adjustment can be made, however the assembly is not loose as the inclusion of springs 1508, 1506 between the head of the bolt 402, 418 and the seat in the washer 404, 408 provide some friction and retain the washer curved ribs 1510, 1516 in the flutes 1228 of the convex frame gutter and the straight ribs 1512 on the vertical adjustment block 406 within the straight flutes 1518 on the convex surface of the gutter. This slight retention force provided by the springs 1508, 1506, when bolts 402, 418 are loosened allows for the Frames 102, 112 to be adjusted through increments of mm and/or degrees, and also provides some tactile feedback regarding the number of mm and degrees of adjustment made. Thus, perpendicular orientation of the flutes eliminates free movement of one type.

For example, adjustment along the AP axis is more controlled as the force applied to make the adjustment moves the parts in the required direction over the curved flutes on the concave frame gutter and maintains the angular position as the parts run along the straight flutes. The control of adjustment is assisted by only loosening one bolt at a time, allowing only two types of adjustment at one time, rather than a possible four if all bolts are loose.

The straight flutes are present on all sizes of the vertical adjustment blocks.

The flutes on the convex side of the frame gutter are arranged in angular increments (degrees), The straight flutes are dependent the precision of the manufacturing process, finer and more precise detail will allow for finer smaller increments of angular adjustment.

The protocol for using the therapeutic position verifying tool may involve at least one of the following steps:
1) Patient is screened and shows signs and symptoms of sleep disorder breathing;
2) The Therapeutic position verifying tool is deployed with any bite method system. Particularly good outcomes may be achieved with the pharyngometer method, which has been shown to be most effective in determining ideal vertical, AP, and lateral dimensions, which are then locked into position for home sleep testing.
3) Patient does first night sleep test for a baseline. The result of the first night sleep test may result in a positive diagnosis for obstructive sleep apnea by the sleep MD. The patient wears the tool the following night during a second sleep test. The results of both sleep tests are sent to the Sleep MD.
4) Based on RDI, REI/AHI measurements from both sleep tests, the sleep MD assesses whether that position will be effective in treating the OSA;
5a) if there is a sufficient favorable response in RDI, REI/AHI measurements, the sleep MD directs dentist to make an oral appliance at that tested position.
5b) if there is no improvement or insufficient improvement, the sleep MD directs the dentist that modification to the position is needed.
6) After the oral appliance is fitted, another sleep test is done with the oral appliance to finalize results, and thereafter, follow ups are done with maintenance recall appointments.

The practitioner of ordinary skill will readily appreciate that the above treatment algorithm is based on sleep times rather than wake times, and thus closely matches the conditions under which the sleep appliance is to be used; thus validating and correlating the use of a pharyngometer to assess all dimensions of occlusion—vertical, lateral and anteroposterior.

The therapeutic position verifying tool is itself a temporary discluding oral appliance that incorporates features to function as a tool for verifying the correct therapeutic position of a permanent OSA oral appliance with which the patient is to be fitted.

Unlike conventional devices, the therapeutic position verifying tool has movement in vertical, AP, lateral pitch and roll dimensions, and those positions are titrated chairside live with the patient. Additionally, the tool allows adjustment of pitch and roll. In embodiments, the dentist may use a pharyngometer to test and screen how the position looks, which eliminates the necessity of repeated titration, requires less guess work and greatly decreases the patient's and doctor's time investment.

The body of the tool may be fabricated from controlled-cure PMMA. The tool can be milled using CAD/CAM digital technology, in which pockets are milled for adjustment assemblies. Controlled Cure PMMA for the stock therapeutic position verifying tool allows for the most strength and durability (compared to cold cured PMMA). Thus, the tool is precise and highly accurate and is also clean because it resists buildup of "biogunk"—deposits of sloughed cells, dried secretions, bacterial growth and old food—found in the oral cavity.

In addition to being sized for different jaws, the tool can be customized chairside to accommodate a patient's unique dentition. In embodiments, cold-cured ortho acrylic such as JET or SNAP may be used for chairside customization. The dentist may size the tool and then do the upper and lower customization by using the acrylic and letting it cure in heated water. Once the acrylic is smoothed and adjusted to feel snug and comfortable, the tool can then be titrated in the vertical, AP, and lateral occlusion dimensions In embodiments, the therapeutic position verifying tool may be locked in a target position and retained in that position for overnight testing. All three dimensions can be adjusted and, if preferred, confirmed by pharyngometer while patient is chairside to obtain the final position.

Using the pharyngometer, the tool can also be used to find or pinpoint the "therapeutic" or target position. The overnight sleep test with that position being tested can also be used to see correlation and efficacy of the pharyngometer bite-taking method.

This final position determined chairside is considered the "START" position of the oral appliance.

The improvement made possible by the therapeutic position verifying tool is that repeated titration to find the therapeutic position won't be needed because the position has already been verified during sleep. Thus, the oral appliance needs to be engineered to that target position. In this way, the correct occlusion can be readily determined to insure that the mandibular/jaw/hyoid position is in the proper therapeutic position and that the oral appliance is the proper remedy to treat that particular patient's OSA.

If other bite registration methods are used the proper position can be measured using a digital caliper with the bite impression taken and those recorded dimensional positions can be transferred to the therapeutic position verifying tool. In such case, the patient still takes a home sleep test with the tool set to that position to allow the sleep MD to determine if that position is effective for that patient. If the dentist was planning on titration to begin with, he or she at least knows ahead of time how much titration will be needed, allowing him/her to gauge the future process more accurately or to have more respect for vertical and lateral occlusion dimensions when considering the bite registration method to be used.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

The invention claimed is:

1. A temporary oral appliance that is reversibly adjustable to assume pre-measured dimensions of occlusion that define a therapeutic position of a permanent oral appliance for treatment of obstructive sleep disorders, wherein the pre-measured dimensions of occlusion include an anterior-posterior axis, a lateral axis, and a vertical axis, an angle of rotation about the anterior-posterior axis, and an angle of rotation about the lateral axis, the temporary oral appliance comprising:
a maxilla frame comprising a maxilla gutter having a convex maxilla gutter bottom surface;
a mandible frame comprising a mandible gutter having a convex mandible gutter top surface;
a vertical adjustment block disposed between said maxilla frame and said mandible frame and comprising a first gutter that is concave and complementary to the convex maxilla gutter bottom surface and a second gutter that is concave and complementary to the convex mandible gutter top surface, said vertical adjustment block shaped to allow adjustment of a spatial relationship between said maxilla frame and said mandible frame according to said pre-measured dimensions by adjusting relative positions of said maxilla frame, said mandible frame and said vertical adjustment block, wherein the spatial relationship includes the angle of rotation about the anterior-posterior axis and the angle of rotation about the lateral axis between the mandible frame and the maxilla frame; and
a first adjustable fastener associated with said maxilla frame and a second adjustable fastener associated with said mandible frame that reversibly fix relative positions of said maxilla frame, said mandible frame and said vertical adjustment block, including fixing the angle of rotation about the anterior-posterior axis and the angle of rotation about the lateral axis between the mandible frame and the maxilla frame.

2. The temporary oral appliance of claim 1, wherein:
each of the maxilla gutter and the mandible gutter defines a slot; and
the maxilla gutter and the mandible gutter are disposed perpendicular to each other.

3. The temporary oral appliance of claim 2, wherein said vertical adjustment block further comprises:
apertures for receiving said first and second adjustable fasteners; and
at least one scale for selecting at least one of the angle of rotation about the lateral axis or the angle of rotation about the anterior-posterior axis.

4. The temporary oral appliance of claim 3, wherein each said adjustable fastener comprises an assembly that includes at least a bolt and a washer, wherein said washer is complementary to a concave side of one of said maxilla gutter or said mandible gutter;
wherein said washer is received by one of said maxilla gutter or said mandible gutter; and
wherein loosening said bolt allows said washer to move within one of said maxilla gutter or said mandible gutter and tightening said bolt restrains movement of said bolt within one of said maxilla gutter or said mandible gutter.

5. The temporary oral appliance of claim 4, further comprising:
flute features disposed within said maxilla gutter and on said convex maxilla gutter bottom surface;
ridges on said washer, wherein interaction of said ridges on said washer with said flute features disposed within said maxilla gutter allows adjustment along either of said anterior-posterior axis and said lateral axis in millimeter increments; and
ridges on said vertical adjustment block, wherein interaction of said ridges on said vertical adjustment block with said flute features on said convex maxilla gutter bottom surface allows adjustment of said rotation about either of said anterior-posterior axis and said lateral axis in single-degree increments.

6. The temporary oral appliance of claim 5, further comprising millimeter scales disposed adjacent to said maxilla gutter to facilitate adjustment along one of said axes.

7. The temporary oral appliance of claim 4, wherein said assembly further includes at least one spring.

8. The temporary oral appliance of claim 4, wherein movement of said bolt within said maxilla gutter disposed in said maxilla frame adjusts said anterior-posterior axis.

9. The temporary oral appliance of claim 4, wherein rotation of said vertical adjustment block about said convex maxilla gutter bottom surface of said maxilla gutter disposed in said maxilla frame adjusts said angle of rotation about said anterior-posterior axis.

10. The temporary oral appliance of claim 4, wherein movement of said bolt within said mandible gutter disposed in said mandible frame adjusts said lateral axis.

11. The temporary oral appliance of claim 4, wherein rotation of said vertical adjustment block about said convex mandible gutter top surface of said mandible gutter disposed in said mandible frame adjusts said angle of rotation about said lateral axis.

12. The temporary oral appliance of claim 3, wherein each said adjustable fastener comprises an assembly that includes at least a bolt and a washer, wherein said washer is complementary to a concave side of said slot disposed in at least one of the maxilla gutter or the mandible gutter.

13. The temporary oral appliance of claim 12, wherein said maxilla and mandible gutters, said vertical adjustment block and said first and second fasteners are provided in a discrete assembly that is bonded with said maxilla frame and said mandible frame.

14. The temporary oral appliance of claim 13, wherein said discrete assembly is fabricated from stainless steel.

15. The temporary oral appliance of claim 12, wherein said maxilla gutter is integral to said maxilla frame and said mandible gutter is integral to said mandible frame.

16. The temporary oral appliance of claim 3, wherein said vertical adjustment block is provided in a plurality of sizes that provide adjustment of a vertical axis in 1 mm increments starting with 0 mm.

17. The temporary oral appliance of claim 1, wherein each of at least said maxilla frame and said mandible frame comprises a body molded from controlled-cure polymer.

18. The temporary oral appliance of claim 1, comprising sets of maxilla and mandible frames in a plurality of sizes.

19. A temporary oral appliance that is reversibly adjustable to assume dimensions of occlusion that define a therapeutic position for treatment of obstructive sleep disorders, wherein the dimensions of occlusion include an anterior-posterior axis, a lateral axis, and a vertical axis, an angle of rotation about the anterior-posterior axis, and an angle of rotation about the lateral axis, the temporary oral appliance comprising:
- a maxilla frame comprising a maxilla gutter that defines a maxilla slot;
- a mandible frame comprising a mandible gutter that defines a mandible slot;
- a vertical adjustment block disposed between said maxilla frame and said mandible frame, said vertical adjustment block comprising:
  - a first gutter that is concave and complementary to a convex curved side of the maxilla gutter; and
  - a second gutter that is concave and complementary to a convex curved side of the mandible gutter;
  - wherein rotation of the vertical adjustment block about the convex curved side of the maxilla gutter adjusts the angle of rotation about said anterior-posterior axis and rotation of the vertical adjustment block about the convex curved side of the mandible gutter adjusts the angle of rotation about the lateral axis; and
- first and second adjustable fasteners, each received into the vertical adjustment block through one of the maxilla slot or the mandible slot, that reversibly fix relative positions of the maxilla frame, the mandible frame and the vertical adjustment block, including fixing the angle of rotation about the anterior-posterior axis and the angle of rotation about the lateral axis between the mandible frame and the maxilla frame.

* * * * *